(12) United States Patent
Varray et al.

(10) Patent No.: US 7,994,280 B2
(45) Date of Patent: Aug. 9, 2011

(54) ON-RESIN PEPTIDE CYCLIZATION

(75) Inventors: Stéphane Varray, Sierre (CH); Oleg Werbitzky, Veyras (CH); Thomas Zeiter, Visperterminen (CH)

(73) Assignee: Lonza AG, Basel (CH)

( * ) Notice: Subject to any disclaimer, the term of this patent is extended or adjusted under 35 U.S.C. 154(b) by 921 days.

(21) Appl. No.: 11/665,537

(22) PCT Filed: Oct. 18, 2005

(86) PCT No.: PCT/EP2005/011182
§ 371 (c)(1),
(2), (4) Date: Nov. 30, 2007

(87) PCT Pub. No.: WO2006/045483
PCT Pub. Date: May 4, 2006

(65) Prior Publication Data
US 2008/0200647 A1    Aug. 21, 2008

(30) Foreign Application Priority Data

Oct. 19, 2004  (EP) ..................................... 04024813
Apr. 25, 2005  (EP) ..................................... 05008979

(51) Int. Cl.
*C07K 1/04* (2006.01)
*C07K 1/06* (2006.01)
*C07K 1/08* (2006.01)

(52) U.S. Cl. ........................................ 530/336; 530/334
(58) Field of Classification Search .................. None
See application file for complete search history.

(56) References Cited

U.S. PATENT DOCUMENTS

| 4,606,856 A | * | 8/1986 | Seyler et al. | 530/307 |
| 5,770,687 A | * | 6/1998 | Hornik et al. | 530/311 |

FOREIGN PATENT DOCUMENTS

| CN | 1 500 805 | 6/2004 |
| WO | 03/093302 | 11/2003 |
| WO | 2004/092202 | 10/2004 |
| WO | 2005/121164 | 12/2005 |

OTHER PUBLICATIONS

Atherton et al. "Peptide Synthesis. Part 7. Solid-phase Synthesis of Conotoxin G1." J. Chem. Soc. Perkin Trans., 1985, 1, 2065-2073.*
Sieber "A new acid-labile anchor group for the solid-phase synthesis of C-terminal peptide amides by the Fmoc method." Tetrahedron Lett., 1987, 28, 2107-2110.*
Eritja et al. "On the use of s-t-butylsulphenyl group for protection of cysteine in solid-phase peptide synthesis using fmoc-amino acids," Tetrahedron, 1987, 43, 2675-2680.*
International Search Report for PCT/EP2005/011182 mailed Apr. 21, 2006.
Annis et al, "Disulfide Bond Formation in Peptides", Methods in Enzymology, vol. 289, pp. 198-221 (1997).

* cited by examiner

*Primary Examiner* — Christina Bradley
(74) *Attorney, Agent, or Firm* — Nixon & Vanderhye P.C.

(57) ABSTRACT

A novel compound of formula I is devised.

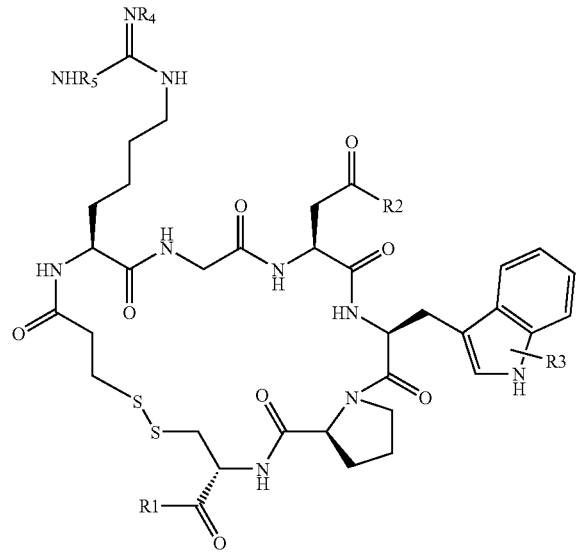

(I)

22 Claims, No Drawings

ON-RESIN PEPTIDE CYCLIZATION

This application is the US national phase of international application PCT/EP2005/011182 filed 18 Oct. 2005, which designated the U.S. and claims benefit of EP 04024813.0 filed 19 Oct. 2004, and EP 05008979.6 filed 25 Apr. 2005, the entire contents of each of which are hereby incorporated by reference.

The present invention relates to a method of disulfide-bond formation in solid phase peptide synthesis (SPPS).

A large variety of protection groups can be employed for protection of cysteine residues, e.g. trityl, acetamidomethyl-, t-butyl, trimethylacetamidomethyl, 2,4,6-trimethoxybenzyl, methoxytrityl, t-butylsulfenyl.

Most commonly, the trityl group is employed for standard cysteine side chain protection during peptide synthesis. For protection of cysteines that are subsequently cyclized to cystine, acetamidomethyl (acm)-protection group along with iodine oxidation has most widely been employed (Kamber et al., 1980, Helv. Chim. Acta 63, 899-915; Rietman et al., 1994, Int. J. Peptide Protein Res. 44, 199-206).

A multitude of oxidating agents other than iodine has been described as allowing of cystine formation in liquid phase cyclization (examples derived from Albericio et al., in: Chan and White, eds., 'FMOC Solid-phase Peptide Synthesis', Oxford university Press 2000, p. 91 to 114: glutathione in aqueous buffer, DMSO, potassium ferricyanide, Ellman's reagent 5,5'-dithiobis-(2-nitrobenzoic acid), iodine, thallium (III)trifluoroacetate, alkyltrichlorosilane-sulphoxide, silver trifluoromethanesulphonate-DMSO mediated oxidation in strongly acidic medium.

Usually, all those methods give rise to undesirable, multiple side-products and require extended reaction times in the range of 10-20 hours for optimum yield.

Volkmer-Engert et al. (J. Peptide Res. 51, 1998, 365-369) describe charcoal-catalyzed oxidative formation of disulfide bonds by using oxygen dissolved in the aqueous solvent. Careful controls were said to prove that the pool of oxygen physically dissolved in the aqueous medium was necessary and sufficient to load the charcoal with oxygen for oxidation. Use of charcoal, as compared to traditional air-sparging in the absence of catalyst, accelerated the reaction rate dramatically.

The use of charcoal inevitably requires to carry out such reaction in homogenous solution but not on-resin; subsequent reaction steps of deprotection would not tolerate the continued presence of charcoal which is impossible to remove from the peptide-resin solid phase though.

WO 03/093302 describes cyclization of a tryptophan containing peptide in solution after release from a solid phase. The peptide has a C-terminal cysteinyl-carboxamide whose side chain thiol function is unprotected and which peptide further is N-terminally derivatized with either a 3-sulfhydryl-propionamide or a 3-[(2-carboxyethyl)dithio]propionamide moiety. Protection and/or deprotection of the cysteine amide side chain is rendered superfluous by side chain anchoring of the peptide on the resin via thioester bonding of said cysteine side chain. N-terminal derivatization with dithio-propionat takes place prior to cleavage from the resin. Cyclization takes place after cleavage from the resin, hence in solution, by means of a disulphide bridge formation between cysteine and the thio-propionamide moiety. Cleavage from the solid support and global deprotection, except for the thiopropionyl function, prior to cyclization is mandatory in this scheme.

As a disadvantage, utmost care must be applied in view of preserving the thio-propionamide moiety during cleavage and global deprotection. Atherton et al. (1985, J. Chem. Perkin Trans. I., 2065) reported that the popular use of thioanisol having dual-function both as scavenger and acidolysis promoter for cleavage from resin also resulted in partial, premature deprotection of acm, tert-butyl and tert-butylsulphenyl protected cysteines. The overall synthetic route is intricate, the many steps involved negatively affecting yields obtainable in this way. Cyclization must be carried out in highly dilute solution to prevent dimerisation. No explicit indication of yields obtained is indeed given in the description.

It is an object of the present invention to devise a more simple and straightforward, other or improved method for synthesizing disulfide-bonded cyclic peptides by means of solid phase synthesis. This object is solved, according to the present invention, by a method of peptide synthesis comprising the steps of a. synthesizing a peptide linked to a solid phase which peptide comprises at least one cysteine, homo- or nor-cysteine residue, which cysteine is protected in its side chain by a S-tert.butyl-sulphenyl group, and b. either coupling N-terminally a further amino acid having a 3-[(2-carboxyethyl)dithio] on its Nα or, optionally, deprotecting the Nα of the N-terminal amino acid and reacting the free Nα with dithio-3,3'-dipropionic acid to yield the corresponding Nα-3-[(2-carboxyethyl)dithio]propionamide, or deprotecting the Nα of the N-terminal amino acid and reacting the free Nα with a compound of formula IV

$$R_7-S-S-[CH_2]_2-COOH \qquad IV$$

wherein R7 is aryl-, aryl- including heteronuclear aryl-, or is aralkyl-, alkylaryl- or alkyl- which may be further substituted with halogeno, amido, ester and/or ether, and c. further reacting the peptide with a S-tert.butyl-sulphenyl-protection group removing reagent, preferably reacting the peptide with a substituted or unsubstituted trisphenyl- or trisalkylphospine, and d. cyclizing the peptide by means of disulfide bond formation between, formally, the cysteine and the 3-thio-propionamide moiety on the Nα, in the presence of air and/or oxygen.

The peptide according to the present invention may be any peptide comprising natural or non-natural amino acids such as e.g. homocysteine, homoarginine, D-cyclohexyl-alanine, Penicillinamide (Pen) or ornithine (Orn). The terms peptide backbone or main chain, side chain and the prefixes 'nor-' 'homo-' are construed in the present context in accordance the IUPAC-IUB definitions (Joint IUPAC-IUB Commission on Biochemical Nomenclature, 'Nomenclature and symbolism for amino acids and Peptides', *Pure Appl. Chem.,* 56, 595-624 (1984). In its more narrow, preferred meaning, 'homo-' amounts to just one extra methylen bridging group in the side chain portion.

Particular attention must be paid to further side-chain protection, in particular when referring to further cysteine, homo- or nor-cysteine residues comprised in the peptide sequence that are intended to remain protected during and not to participate in the cyclization reaction. Preferably, such further sulfhydryl-moiety comprising residues are protected by non-trialkylphosphine sensitive protection groups, more preferably, such non-sensitive sulfhydrylprotection group is selected from the group comprising trityl-, tert.butyl-, acetamidomethyl-, alkylated acetamidomethyl-, alkylated trityl-protection groups. On the general level, side chain protection groups as commonly employed in the art (see e.g. Bodansky, M., *Principles of Peptide Synthesis,* s. below) may be used to protect susceptible side chains which could otherwise be modified in the coupling and deprotection cycles. Examples of amino acids with susceptible side chains are Cys, Asp, Glu, Ser, Arg, Homo-Arg (Har), Tyr, Thr, Lys, Orn, Pen, Trp, Asn and Gln. Alternatively, a post solid-phase synthesis chemical modification of the peptide amide may be carried out to yield a desired side chain. For instance, as set forth amply in different references (EP-301 850; Yajima et al., 1978, J. Chem. Cos. Chem. Commun., p. 482; Nishimura et al., 1976, Chem. Pharm. Bull. 24:1568), homoarginine can be prepared by guanidation of a lysine residue comprised in the peptide chain or an arginine can be prepared by guanidation of an ornithine residue comprised in the peptide chain, though this is a less preferred, more laborious option only. Notably, coupling e.g. of Har requires extended coupling times and replenishing of coupling reagents. According to the present invention, it is one preferred embodiment to couple Arg or Har, preferably when being used as FMOC-Arg and FMOC-Har respectively, without the use of side chain protecting groups. This may be achieved by ensuring that post-coupling of the individual Arg or Har residue, the guanidino moiety is quantitatively protonated prior to any further coupling reactions and forms stable ion pair with the proton donor in organic solvent. This is preferably achieved by treating the resin bound peptide amide with an excess of the acidic coupling auxilliary BtOH or the like as described as one preferred embodiment in more detail below in the experimental section. Another example of scavenging the charge of the guanidinium group is to use tetraphenyl borate salts of Fmoc-protected HAR for synthesis as set forth in U.S. Pat. No. 4,954,616.

Examples of suitable protection groups for individual amino acid side chains occurring in preferred embodiments of the peptide according to the present invention are:

Preferably, the arginine side chain may be optionally covalently protected during synthesis e.g. with tosyl, benzyloxycarbonyl, pentamethylenchromanesulfonyl (Pmc), pentamethyldihydrobenzofuransulfonyl (Pbf), 4-methoxy-2,3,6-trimethylbenzenesulfonyl (Mtr) and its 4-tbu-2,3,5,6-tetramethyl homologue (tart), adamantyloxycarbonyl or Boc. Pmc, Pbf, Mtr or Tart are strongly preferred for protecting Arg, most preferably it is Pbf.

Trp is preferably protected during synthesis with Boc. Optionally, it may be N-protected with formyl or sym-mesitylene-sulfonyl.

Suitable carboxylic acid side chain protection groups, by way of esterification of the side chain carboxy group, are e.g. adamantyl, tert.butyl, allyl, benzyl (Z), preferably the carboxy group is protected by conversion into a tert.butyl ester. It goes without saying that the removal of the cited protection groups may require different deprotection chemistries, as is well-known (see Bodansky, M., below).

The solid phase support or resin may be any support known in the art that is suitable for use in solid-phase synthesis. This definition of solid phase comprises that the peptide is bonded or linked via a functional linker or handle group to the solid phase or resin, such linker being implied when speaking of 'solid-phase' in the present context. Example of solid-phases are e.g. polystyrene supports which may be further functionalized with e.g. p-methylbenzyl-hydrylamine for instance, or rigid functionalized supports such as Kieselgur-encapsulated poly-dimethylacrylamide (pepsyn K), silica or controlled pore glass. The resin matrix of the solid-phase may also be constituted by an amphipilic polystyrene-PEG resin (e.g. Tentagel, see U.S. Pat. No. 4,908,405) or PEG-polyamide or PEG-polyester resin, e.g. Kempe et al., J. Am. Chem. Soc. 1996, 118, 7083; also cp. U.S. Pat. No. 5,910,554, US2003078372 A1. Purity of product obtained on such mixed PEG resins is better than on traditional resins, however resin loading is usually less efficient and/or chemical stability in particular in acidic media is oftenly not satisfactory. Polystyrene-PEG resins are reaching higher loadings, but lower amphiphilicity is obtained because the PEG contents is decreased.

Preferably the solid support is based on a polystyrene, PEG such as e.g. especially an amphiphilic PS-PEG or a polydimethylacrylamide polymer matrix or resin.

According to the present invention, the peptide may be bonded via an amino acid side chain, typically the side chain of the C-terminal amino acid unless such amino acid is the very one S-tBu-sulphenyl-protected cysteine residue according to the present invention, or may be bonded via the C-terminal α-carboxy group to a resin via an ester, thioester or amide bond. Examples are solid supports having amino-methyl, carboxyl or bromomethyl or iodomethyl radicals for instance or which supports are derivatized by known linker or handles such as e.g. Wang, trityl, 2-chloro-trityl-, 4-methoxytrityl-, 'Rink amide' 4-(2',4'-dimethoxybenzyl-aminomethyl)-phenoxy-, Sieber resin 9-amino-6-phenylmethoxyxanthen-, 4-hydroxymethylphenoxyacetyl- or 4-hydroxymethylbenzoic acid (the latter requiring attachment of the first amino acid by means of p-dimethylaminopyridine catalysed esterification protocol than can result in racemisation of susceptible amino acids, e.g. Trp and in particular cysteine, see Atherton, E. et al., 1981, J. Chem. Soc. Chem. Commun., p. 336 ff) linker. Methods of providing thioester linkages to a resin are disclosed in detail and are further referenced in WO 04/050686. In one preferred embodiment of the present invention, thioester linkages for bonding of the peptide moiety to the solid-phase are disclaimed hence being vulnerable to 20% piperidine and further to treatment with nucleophils such as trisphenylphosphine.

Rink amide, Sieber resin (Tetrahedron Lett. 1987, 28, 2107-2110) or similar 9-amino-xanthenyl-type resins, PAL resins (Albericio et al., 1987, Int. J. Pept. Protein Research 30, 206-216) or the specially substituted trityl-amine derivatives according to Meisenbach et al., 1997, Chem. Letters, p. 1265 f.) are examples of a linker or handle from which a Cα-carboxamid is generated or liberated upon cleavage of the peptide from the resin or solid phase. It goes without saying that use of such amide linkers is of course dependent on the type of solid phase synthesis carried out, ie. whether is traditional Boc or now customary, orthogonal Fmoc protection chemistry that is used for coupling; Boc-specific amide resin linker is PAM, for instance. Accordingly, solid phases comprising such linker groups are termed 'amide-producing solid phases' in the present context.

Preferably, the peptide is anchored to the solid phase by either an amide or ester bond via the C-terminus. More preferably, the solid phase is an acid-sensitive or acid-labile solid phase with regard to cleavage of the peptidyl moiety from the solid phase, even more preferably, it is an amide generating acid-labile solid-phase. Such acid-labile solid phases require at least 0.1% trifluoroacetic acid (TFA), more preferably at least 0.5% TFA in a polar aprotic solvent for cleavage from resin. Most preferably, the solid-phase is an acid-sensitive solid phase that is cleaved under weakly acidic conditions, that is 0.1 to 10% TFA in said solvent are sufficient to effect at least 90% cleavage efficiency upon incubation at room temperature up to 5 hours. Such highly acid-labile solid phase are e.g. 2-chlorotrityl resins, Sieber resin, PAL resin or 4-(4-hydroxymethyl-3-methoxyphenoxy)-butyric acid (HMPB) resin, Sieber and Rink giving rise to C-terminally amidated peptide upon acidolysis. Such acid-labile solid phases are particularly vulnerable to on-resin deprotection chemistries for side-chain protection groups and hence particular attention must be paid in these cases.

In case of side chain anchoring via C-terminal cysteine residue to the handle group of a solid support, the linking bond must be a thioether or thioester bond. Further suitable residues for side-chain anchoring are carboxy groups of acidic side chains, hydroxy groups and in particular the ε-amino group of lysine. It goes without saying that in case of side chain anchoring, generally the C-terminal free carboxy-group is to be protected by esterification or amidation prior to carrying out the first coupling reaction, e.g. by using FMOC-Lys-carboxamid for linking reaction of the side chain amino function to the solid phase.

In a preferred embodiment, the S-tert.butyl-sulphenyl protected cysteine is the C-terminal residue of the peptide and is bonded via the carboxy-terminus by means of an ester or amide bond to the solid phase, with the proviso, that said linking bond is not a benzylester moiety but preferably is an acid-labile resin that is cleaved under weakly acidic reaction conditions as defined above. A C-terminal cysteine is particularly prone to subject to racemisation in acidic conditions.

Removal of S-tert.butyl-sulphenyl protection groups from cysteine by means of reaction with tertiary phosphines has been described, for instance by using tributylphosphine (Atherton et al., 1985, J. Chem. Soc., Perkin I. 2057) and triethylphosphine (Huang et al, 1997, Int. J. Pept. Protein Res. 48, 290). The same deprotection step is, according to the present invention, employed to cleave the disulfide bond of the Nα-3-[(2-carboxyethyl)dithio]propionamide, its homologues having a different number of methylene groups or of the compound of formula IV. The tert-butylsulphenyl group is most oftenly cleaved by means of thiol reagents such as e.g. β-mercapto-ethanol or dithio-threitol (DTT) or tertiary phosphines (Huang et al., 1997 Int. J. Pept. Protein Res. 48, 290; Rietmann et al., 1985, Recl. Tray. Chim. Pays-Bas, 1141). Preferably, the tertiary phosphine is triphenylphospine or is an alkylated or alkoxylated triphenylphosphine, such as e.g. tri-(p-methoxyphenyl)-phosphine or even more preferably is a trialkylphosphine wherein the alkyl may be the same or different, and wherein each alkyl is a C1 to C7 alkyl, preferably C1 to C4, and may be branched or linear alkyl. Preferably, the alkyl is linear. Examples are methyl, ethyl, propyl, i-propyl, n-butyl, i-butyl. Tri-n-butyl-phosphine and tri-ethylphosphine are particularly preferred. The alkyl may optionally be further substituted with halogeno, methoxy or ethoxy or, where amenable with the solvent system, carboxy or is, preferably, unsubstituted. Surprisingly, according to the present invention, it has unexpectedly been found that disulfide cleavage by means of phosphines may also be used with the very acid-labile resins cleavable in weakly acidic reaction conditions such as Sieber or 2-CTC resin, for instance. It is often overlooked that thiol reagens reduce and hence cleave disulfides by forming disulfide products themselves. Whereas in case of DTT, intramolecular ring closure is favored, in case of β-mercaptoethanol, any intramolecular reaction product, e.g. by way of disulfide exchange reaction, is feasible. Further then, even newly formed disulfides may undergo further exchange reaction. The widespread use of thiol reagents apparently owes to the fear of side reactions such as e.g. leakage from resin when using tertiary phosphine reagents.

Coupling reagents for peptide synthesis are well-known in the art (see Bodansky, M., Principles of Peptide Synthesis, $2^{nd}$ ed. Springer Verlag Berlin/Heidelberg, 1993; also see discussion of role of coupling additives or auxiliaries therein). Coupling reagents may be mixed anhydrides (e.g. T3P: propane phosphonic acid anhydride) or other acylating agents such as activated esters or acid halogenides (e.g. ICBF, isobutyl-chloroformiate), or they may be carbodiimides (e.g. 1-ethyl-3-(3-dimethylaminopropyl)-carbodiimide), activated benzotriazin-derivatives (DEPBT: 3-(diethoxyphosphoryloxy)-1,2,3-benzotriazin-4(3H)-one) or uronium or phosphonium salt derivatives of benzotriazol.

In view of best yield, short reaction time and protection against racemization during chain elongation, more preferred is that the coupling reagent is selected from the group consisting of uronium salts and phosphonium salts of the benzotriazol capable of activating a free carboxylic acid function along with that the reaction is carried out in the presence of a base. Suitable and likewise preferred examples of such uronium or phosphonium coupling salts are e.g. HBTU (O-1H-benzotriazole-1-yl)-N,N,N',N'-tetramethyluronium hexafluorophosphate), BOP (benzotriazole-1-yl-oxy-tris-(dimethylamino)-phosphonium hexafluorophosphate), PyBOP (Benzotriazol-1-yl-oxy-tripyrrolidinophosphonium hexafluorophosphate), PyAOP, HCTU (O-(1H-6-chloro-benzotriazole-1-yl)-1,1,3,3-tetramethyluronium hexafluorophosphate), TCTU (O-(1H-6-chlorobenzotriazole-1-yl)-1,1,3,3-tetramethyluronium tetrafluoroborate), HATU (O-(7-azabenzotriazol-1-yl)-1,1,3,3-tetramethyluronium hexafluorophosphate), TATU (O-(7-azabenzotriazol-1-yl)-1,1,3,3-tetramethyluronium tetrafluoroborate), TOTU (O-[cyano(ethoxycarbonyl)methyleneamino]-N,N,N',N''-tetramethyluronium tetrafluoroborate), HAPyU (O-(benzotriazol-1-yl)oxybis-(pyrrolidino)-uronium hexafluorophosphate.

Preferably, when using DEPBT or the like, uronium or phosphonium salt reagents, a further or second weak base reagent is needed for carrying out the coupling step. This is matched by a base whose conjugated acid has a pKa value of from pKa 7.5 to 15, more preferably of from pKa 7.5 to 10, with the exclusion of an α-amino function of a peptide or amino acid or amino acid derivative, and which base preferably is a tertiary, sterically hindered amine. Examples of such and further preferred are Hünig-base (N,N-diisopropylethylamine), N,N'-dialkylaniline, 2,4,6-trialkylpyridine or N-alkyl-morpholine with the alkyl being straight or branched C1-C4 alkyl, more preferably it is N-methylmorpholine or collidine (2,4,6-trimethylpyridine), most preferably it is collidine. Examples of C1-C4 alkyl are e.g. methyl, ethyl, n-propyl, isopropyl, n-butyl, tert.butyl, isobutyl.

The use of coupling additives, in particular of coupling additives of the benzotriazol type, is also known (see Bodansky, supra). Their use is particularly preferred when using the highly activating, afore said uronium or phosphonium salt coupling reagents. Hence it is further preferred that the coupling reagent additive is a nucleophilic hydroxy compound capable of forming activated esters, more preferably having an acidic, nucleophilic N-hydroxy function wherein N is imide or is N-acyl or N-aryl substituted triazeno, most preferably the coupling additive is a N-hydroxy-benzotriazol derivative (or 1-hydroxy-benzotriazol derivative) or is an N-hydroxy-benzotriazine derivative. Such coupling additive N-hydroxy compounds have been described in large and wide in WO 94/07910 and EP-410 182 and whose respective disclosure is incorporated by reference hereto. Examples are e.g. N-hydroxy-succinimide, N-hydroxy-3,4-dihydro-4-oxo-1,2,3-benzotriazine (HOOBt), 1-hydroxy-7-azabenzotriazole (HOAt) and N-hydroxy-benzotriazole (HOBt). N-hydroxy-benzotriazine derivatives are particularly preferred, in a most preferred embodiment, the coupling reagent additive is hydroxy-3,4-dihydro-4-oxo-1,2,3-benzotriazine.

Ammonium salt compounds of coupling additives are known and their use in coupling chemistry has been described, for instance in U.S. Pat. No. 4,806,641.

In a further particularly preferred embodiment, the uronium or phosphonium salt coupling reagent is an uronium salt reagent, preferably it is HCTU, TCTU or HBTU, more preferably it is HCTU or TCTU, and most preferably it is used in the reaction in combination with N-hydroxy-3,4-dihydro-4-oxo-1,2,3-benzotriazine or a salt thereof. This embodiment is mainly preferred for use in chain elongation step of peptide synthesis after removal of the base-labile Nα-protection group, but may as well be used for lactamization reaction during side-chain cyclization.

In the context of the present invention, it is to be noted that HCTU and TCTU are defined as to be encompassed by the term 'uronium salt reagent' despite that these compounds and possible analogues have been shown to comprise an isonitroso moiety rather than an uronium moiety by means of crystal structure analysis (O. Marder, Y. Shvo, and F. Albericio "*HCTU and TCTU: New Coupling Reagents: Development and Industrial Applications*", Poster, Presentation Gordon Conference February 2002), an N-amidino substituent on the heterocyclic core giving rise to a guanidium structure instead. In the present context, such class of compounds is termed 'guanidium-type subclass' of uranium salt reagents according to the present invention.

Deprotection of the base labile Nα may be carried out as routinely done in the art, e.g. with 20% piperidine in N-methyl morpholine in case of Fmoc chemistry. Most widely, Fmoc or Boc protection chemistry for the N-terminus is routinely applied in solid phase synthesis but further optional Nα protection chemistries are known in the art and can be app lied where not interfering with the present invention to devise disulfide-borne peptide cyclization of the resin-conjugated peptide.

The afore said coupling chemistry can also be employed for coupling of the compound of formula IV, $R_7$—S—S—$[CH_2]_2$—COOH as defined above. This compound can easily be produced e.g. by reacting the respective symmetric carboxylic acid imide e.g. with an alkanol or alkylamine.

Cyclization is carried out according to the present invention in the presence of a first weak base in a polar, aprotic organic solvent. The oxdidating reagent mediating cyclization may be any mentioned in Chan and White, eds., 'FMOC Solid-phase Peptide Synthesis', Oxford university Press 2000, p. 91 to 114: glutathione in aqueous buffer, DMSO, potassium ferricyanide, Ellman's reagent 5,5'-dithiobis(2-nitrobenzoic acid), iodine, thallium (III) trifluoroacetate, alkyltrichlorosilane-sulphoxide, silver trifluoromethanesulphonate-DMSO mediated oxidation in strongly acidic medium where not being entirely impractical for use in on-resin cyclization in a furthermore organic solvent system for solvation of protected peptide such as is charcoal mediated oxidation. Another general method is the use of carboethoxysulfenyl chloride for disulfide bond formation (Le-Nguyen, D., 1986, Int. J. Peptide Protein Res. 27, 285-292). For reason of solvent system, in one preferred embodiment cyclization is carried out by DMSO mediated oxidation as described e.g. in U.S. Pat. No. 5,144,006 in more detail, rendering DMSO both an oxidans and a miscible co-solvent in addition to the below mentioned solvents, eventually in the presence of minor amounts of water. DMSO provides acceptably fast reaction rates, is a denaturing co-solvent and helps to solubilize the peptide substrate. Given its oxidizing effect on methionine side chains, its use in on-resin cyclization, prior to deprotection of amino acid side chains, is much more convenient than its normal use in solution with deprotected peptides.

In a most preferred embodiment said cyclization is carried out in the presence of air and/or oxygen but notably in the absence of a heterogenous, rate-accelerating catalyst, for achieving oxidation of the thiol groups in order to form disulfide bonds. Preferably, the cyclization is carried out substantially catalyst-free, that is in the absence of an catalytically effective or substantial amount of a heterogenous catalyst.

According to the present invention and in particular when being carried out with air and/or oxygen as the oxidating reagent, more preferably with air/oxygen in the absence of said heterogenous or solid-phase catalyst, the cyclization step according to the present method is remarkably efficient and requires only about 0.5 to 2 hours reaction time, allowing of literally quantitative, complete conversion of educt to the desired product under very mild reaction conditions (ambient temperature typically, expedient temperature range being 10° C. to 80° C. though reflux temperature of solvent must be taken into account of course). Unprecedently, conversion is complete still then. This is an outstanding achievement and has not yet been achieved in disulfid-bonding driven cyclization of peptide, nor have such simple, mild and rapid cyclization reaction conditions been devised earlier. No tedious mixing and separation problems for a heterogenous catalyst arise ever. Still, the reaction rate completely parallels that of the catalyst-borne reaction of the prior art. Due to the straightforward course of reaction, formation of side products is almost entirely avoided.

Suitable polar, aprotic solvents are e.g. acetonitril, dimethylformamide, dichloromethane, N-methyl-pyrrolidone, tetrahydrofurane. In contrast to water, such solvent usually may not physically dissolve relevant amounts of oxygen to supply the oxidative formation of disulfide bonds as has been described for aqueous catalyst systems before.

Accordingly, the supply of air, air/oxygen or pure oxygen must be paid attention to. Air/oxygen may be supplied by thorough stirring, vortexing, special design of propellers used for stirring, gas sparging into the liquid. The gas may be air or pure oxygen or air enriched with oxygen. In one particularly preferred embodiment, large surface areas of the bottom and/or walls of the reactor vessel are punctured as to sparge gas into the liquid, under thorough stirring.

It is also possible that different protection modes for cysteines are used on the one peptide of the present invention. For instance, further cysteines in the peptide chain may be protected traditionally by acm protection groups, for providing of further regiospecific disulfide bond in between internal cysteines by means of standard iodine oxidation in solution after cleavage from resin, and after initial disulfide bonding according to the present invention took place on-resin.

The first weak base reagent is a weak base whose conjugated acid has a pKa value of from pKa 7.5 to 15, more preferably of from pKa 8 to 10, preferably, it is a tertiary, sterically hindered amine. Examples of such and further preferred are Hünig-Base (N,N-diisopropylethylamine), N,N-dialkyl-aniline, 2,4,6-trialkylpyridine or N-alkyl-morpholine with the alkyl being straight or branched C1-C4 alkyl such as methyl, ethyl, n-propyl, i-propyl, n-butyl, most preferably it is N-methylmorpholine, collidine (2,4,6-trimethylpyridine) or Hünig-Base.

Preferably the prior removal of the disulfide protection groups, notably the removal of the S-tert.butyl-sulphenyl group, is effected in the presence of a first weak base reagent for avoiding any risk of leakage from the resin by minor acidolysis, that is at a pH of from 7.5 to 12, more preferably of from 8 to 11. Optionally, by using polar aprotic solvents such as THF or acetonitril that are freely miscible with water, basic salts such as e.g. sodium acetate in aqueous solution may be used for that purpose. This embodiment is particularly preferred when using tertiary phosphines for said disulfide group cleavage or removal step. By combining a suitable oxygen supply concomittant with such disulfide protection group removal, it may be possible in another embodiment of the present invention, e.g. when using polar, aprotic organic solvent along with oxygen supply in the presence of a tertiary amine and when using tertiary phosphine for deprotection that is inert to oxygen, to carry out both disulfide deprotection and cyclization not only in a one-pot reaction but even as a single reaction step.

Since the present method allows of on-resin cyclization, it further does not require tedious and yield-decreasing strong dilution of peptide for favoring intra-over intermolecular cyclization as previously required in most methods described in the prior art. The on-resin operation mode of the invention allows of quick and efficient intra-molecular cyclization only, giving no chance of dimerization at all.

In a further preferred embodiment, the peptide is the peptide of formula I. The term protection group is to be construed as being protection group for a given side chain functionality or specific side chain which protection group is compliant with being used in standard tert-butyloxycarbonyl (Boc) or 9-fluorenylmethoxycarbonyl (Fmoc) solid phase peptide synthesis. Such protection groups and the use of specific protection groups for specific side chain functionalities is well-known in the art and is routine (s. Chan et al., ed., supra; Bodansky et al. supra).

In one further possible embodiment, the peptide is optionally synthesized on a solid phase not by permanent, covalent attachment of the peptidyl moiety to a solid-phase but by non-covalent, reversible attachment to the solid-phase by means of a stable metal chelate complex (product news jointly from Lonza AG, Basel, Switzerland and AplaGen GmbH, Baesweiler, Germany, October 2004), similar to the established hexa-His tag technology employed in protein purification. Such non-covalent solid-phase linkage or similar, future embodiments are encompassed by the present invention as well and the preferred mode of operating the present invention set forth above and below apply to this embodiment as well.

Suitable solid-phase conjugated, favorably cyclized peptides as described in the foregoing, and their combination with the above and below cited preferred embodiments, are further objects of the present invention.

A first object is a peptide of formula I

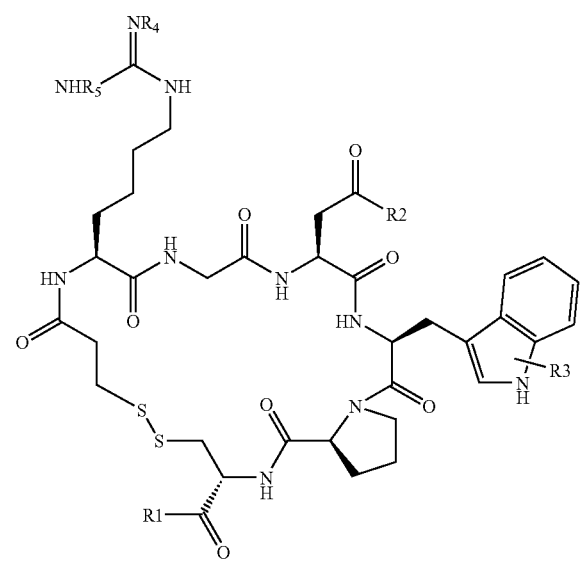

wherein R4, R5 are H or an Arg-protection group, R2 is a carboxylic acid protection group and R3 is a Trp-protection group and R1 is a solid phase in a thioester, ester or amide bond linkage to the peptide backbone.

Preferably, in such peptide R4, R5 are H and R3 is N-benzyl-oxycarbonyl and R2 is tertiary-butyl.

Preferably, said solid phase is a Sieber resin or other resin comprising an amide-generating linker or handle which is consequently in amide bond linkage to the peptide backbone.

A second object is a peptide, preferably a peptide comprising at least one amino acid side chain protection group, wherein the peptide is linked to a solid phase via the C-terminal residue or via an amino acid side chain, characterised in that the peptide is a cyclic peptide comprising a moiety of formula II

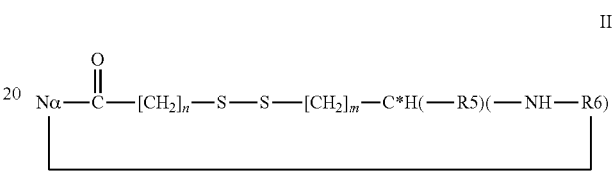

wherein n,m are independently selected from the range of 1 to 10, preferably n=2 and m=1 (yielding a cysteinyl moiety), Nα is the N-terminal nitrogen of the peptide backbone and C* is the Cα of an amino acid residue of the peptide backbone, with R6 being the N-terminal, cyclic half of the peptide backbone that is terminating with said Nα and R5 being the C-terminal half of the peptide backbone that is linked to the solid phase, with the proviso that N≠Nα, and preferably wherein R6 comprises at least 3, more preferably at least 4 intervening amino acid residues. For the sake of clarity, R5 is to be construed as to amount to C*H(—CO—NH—R') or C*H(—CO—R') or eventually C*H(—CO—S—R'), R' comprising a solid phase possibly including a linker or handle, R5 and optionally a number of amino acid residues linked to said solid-phase. Preferably, R5 and R6 comprise up to 200, more preferably up to 100, most preferably up to 50 amino acid residues.

A further object is a peptide, preferably a peptide comprising at least one amino acid side chain protection group other than a S-tert.butyl-sulphenyl group on a cysteine, homo- or nor-cysteine residue, which peptide is linked to a solid phase via the C-terminal residue, characterised in that the peptide comprises at least one cysteine, homo- or nor-cysteine residue that is protected in its side chain by a S-tert.butyl-sulphenyl group and which is N-terminally substituted at its Nα to constitute the amide moiety of formula III

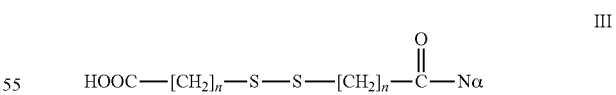

wherein n=1 to 10, preferably n=2.

Again a further object is a peptide, preferably a peptide comprising at least one amino acid side chain protection group other than a S-tert.butyl-sulphenyl group on a cysteine, homo- or nor-cysteine residue, which peptide is linked to a solid phase via the C-terminal residue, characterised in that the peptide comprises at least one cysteine, homo- or nor-cysteine residue that has a free thiol group in its side chain and which is N-terminally substituted at its Nα to constitute the amide moiety of formula III

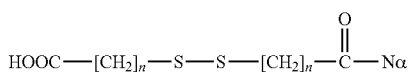

$$HOOC-[CH_2]_n-S-S-[CH_2]_n-\overset{O}{\underset{\|}{C}}-N\alpha \qquad \text{III}$$

wherein n=1 to 10, preferably n=2.

Likewise, said peptides of the last and second last object of the present invention again preferably comprise up to 200, more preferably up to 100, most preferably up to 50 amino acid residues. It goes without saying that the choice of resin will also impact the yield obtained when synthesizing very long peptides, if not even being a prerequisite for synthesizing peptides of 100 amino acid residues and more. PEG resins, for instance, may be usually a good choice for such. Further it goes without saying the peptide's individual amino acid sequence may well influence maximum chain length and coupling efficiency obtainable with a given peptide; widely known example is unfavorable interchain aggregation of peptide threats during linear synthesis due to beta-sheet formation and interchain bonding.

EXPERIMENTS

Eptifibatide was chosen as a protected model peptide for on-resin cyclization, seeking to devise the novel, improved method of the present invention; a solid-phase synthesis method for eptifibatide has been described in U.S. Pat. No. 5,318,899 before.

The overall synthetic strategy is set forth in table I underneath (wherein product is SEQ ID NO:1).

TABLE I

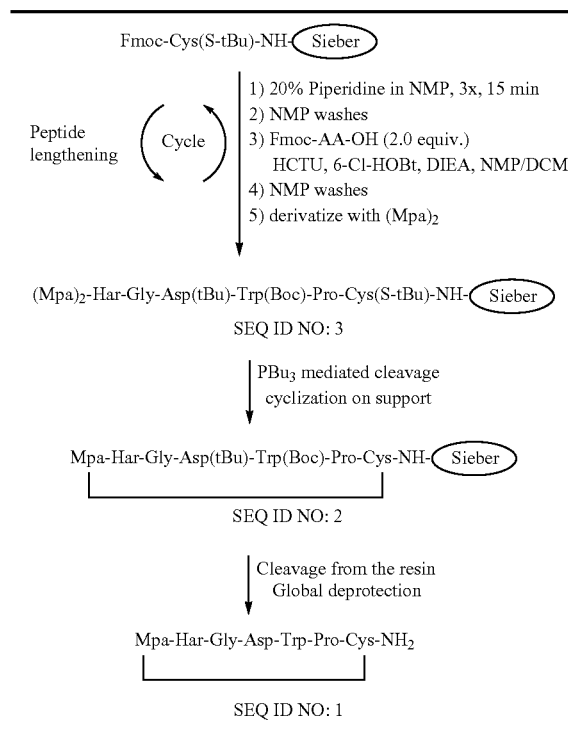

1.1 FMOC SPPS of linear peptide Gly-Asp(tBu)-Trp(Boc)-Pro-Cys(S-tBu)-Sieber (residues 4-8 of SEQ ID NO:3)

Synthesis of FMOC-Cys(S-tBu)-OH has been described before (Rietman et al., 1994, Synth. Commun. v 24, p. 1323 f). Sieber resin was a Novabiochem product and was purchased from Calbiochem-Novabiochem (belonging to EMD Biosciences, California/U.S.A.). All FMOC amino acids, including FMOC-Cys(S-tBu)-OH (cat. No. B-1530) were purchased from Bachem AG (Bubendorf, Switzerland).

Loading of resin was at 0.52 mmol/g and of a total of 10 g Sieber resin. Coupling time for loading was twice the standard coupling time, namely 60 min. in total. Couplings were conducted with 2 eq. each of respective amino acid in the presence of 1 eq. each of 6-chloro-HOBt, TCTU, Hünig-Base (Disopropylethylamine), in dichloromethane. Washes were with N-methyl-pyrrolidone (NMP).

FMOC deprotection was done by 3 cycles of 15 min. 10% piperidine in N-methyl-pyrrolidone; efficiency of cleavage and completion of synthesis was analysed by Ninhydrin reaction and reverse phase HPLC, respectively.

1.2 Elongation of peptide from 1.1 to Har-Gly-Asp(tBu)-Trp(Boc)-Pro-Cys(S-tBu)-Sieber (residues 3-8 of SEQ ID NO:3)

The coupling of the FMOC-Har residue (Bachem, Burgendforf, Switzerland) took place in the presence of 1 eq. HOBt per eq. amino acid (for keeping the Guanidino group protonated); the FMOC amino acid was preincubated with HOBt and 1-eq. diisopopyl-carbodiimid in NMP and was then mixed with the resin. Har coupling took 180 min. (other aa: 30 min.) followed by a second cycle with replenished reagents of about 60 min. In this way, standard 99.8% coupling efficiency as for the other residues could be matched. FMOC cleavage took place as before. Notably, after FMOC cleavage und subsequent NMP washes, repeated washing with HOBt was done to prevent further swelling of the resin.

Note: Prolongated coupling using TCTU is also feasible for Arg coupling using no protection group other than above ion-pairing with HOBt. Further Ion pairing with HOBt is a preferred embodiment as compared to using covalently coupled protection chemistry for Arg, such as e.g. Pbf, which may be problematic regarding side reactions during deprotection.

1.3 Derivatization of peptide resin from 1.2 to (Mpa)-2-Har-Gly-Asp(tBu)-Trp(Boc)-Pro-Cys(S-tBu)-Sieber (SEQ ID NO: 3)

Reaction with dithio-3,3'-dipropionic acid (Novabiochem) took place in DMF cooled to less than 10° C. in an ice bath. 1 eq. of diisopopyl-carbodiimid was added to the reaction mixture over 10 min. with stirring, whilst controlling the temperature to stay below 15-20° C. Thereafter, the reaction mixture was added to the deprotected, resin-bound peptide product from section 1.2. Coupling was allowed to proceed for 6 hours at ambient temperature.

Aliquots of reaction product were cleaved from the resin with 60% TFA and analyzed by LC-(electrospray) MS. Conversion was quantitative, though two major product peaks were detected (<25% sideproduct: dipeptide). Hence the yield for this step was >75%.

1.4 Deprotection with $Bu_3P$

The resin was suspended and washed three times in tetrahydrofurane (THF). The reaction was carried out for 1 h at room temperature with 50 eq. tributylphosphine made up as 19% (v/v) $PBu_3$/77% (v/v) THF/4% (v/v) saturated aqueous solution of sodium acetate; precipitating salt was filtered off prior to use. Reaction proceeded uniformly to give one dominant product peak. The yield was determined by reverse phase HPLC and was found to amount to 98.9% pure product.

1.5 Cyclization to yield Mpa-Har-Gly-Asp(tBu)-Trp(Boc)-Pro-Cys-Sieber (SEQ ID NO: 2)

| Time | Acetonitrile (0.1% TFA) | Water (0.1% TFA) |
|---|---|---|
| 0 | 60 | 40 |
| 5 | 97 | 3 |
| 16 | 97 | 3 |
| 17 | 60 | 40 |

The peptide-resin conjugate from 1.4 was washed swollen and washed three time in NMP. Cyclization was done by incubating the resin for 1 h at room temperature with 6% DIEA (Hünig-Base) in NMP; reaction was carried out in a vertical glass vessel which comprised a horizontally bisecting, sealed-in G3 (16-40 µm) glass frit in its lower portion. The glass frit or fritted plate was vented with air from below, allowing of air bubbling across the entire cross-section of the solvent-covered reactant space above the frit in which the resin was floating by the bubbling air from underneath. A strictly pure, uniform product is obtained, no distinct or shattered sideproducts do show off after this reaction step. The conversion to product was 100%, as determined independently by both reverse phase HPLC and LC-MS. RP-HPLC was carried out on a Hypersil-Keystone™ Betabasic (Thermo Electron Corp., Waltham Mass./U.S.A.) C18 150×4.6 mm column, with an injection volume of 15 µl and detection at 262 nm at a column temperature of 35° C. Gradient run is

1.6 Global Deprotection

Global deprotection is prepared by swelling the resin three times in dichloromethane (DCM). Cleavage reaction phase mixture is prepared as to be made up from
- 86.5% TFA (785 eq.)
- 4.5% Thioanisol (36.5 eq.)
- 3% Phenol (32.4 eq.)
- 3% DCM (38 Eq.)
- 3% H2O (178 Eq.)

Reaction takes place at 15° C. for 2 h on an slowly rotating orbital shaking device. Reaction is terminated and product is precipitated, after filtering off the resin, by dropwise addition of tert.butyric acid methyl ester. The product is a uniform peak; no major sideproduct can be detected. the above conditions of global deprotection have been tested on a control and found not to affect preformed disulfide bridges in peptides. Conversion in this last step is >99%, as determined by RP-HPLC and LC-MS as set forth in detail in section 1.5 above.

The invention claimed is:

1. Method of peptide synthesis, comprising the steps of
   a) synthesizing a peptide linked to a solid phase which peptide comprises at least one cysteine, homo- or norcysteine residue, which cysteine is protected in its side chain by a S-tert.butyl-sulphenyl group and wherein said cysteine is the last C-terminal residue, wherein said S-tert.butyl-sulphenyl protected C-terminal cysteine is bonded via the carboxy-terminus by means of an ester or amide bond to the solid phase, with the proviso, that said linking bond is not a benzylester bond, but is an acid-labile bond that is cleaved under weakly acidic reaction conditions,
   b) either coupling N-terminally a further amino acid having a 3-[(2-carboxyethyl)dithio]propionyl-radical- on its Nα or deprotecting the Nα of the N-terminal amino acid and reacting the free Nα with dithio-3,3'-dipropionic acid to yield the corresponding Nα-3-[(2-carboxyethyl)dithio]propionamide or deprotecting the Nα of the N-terminal amino acid and reacting the free Nα with a compound of formula IV

R7-S—S—[CH$_2$]$_2$—COOH IV wherein R7 is aryl-, including heteronuclear aryl, or is aralkyl-, alkylaryl- or alkyl-, which may be further substituted with halogeno, amido, ester, carboxy or ether, and
   c) reacting the peptide with a S-tert.Butyl-sulphenyl-protection group removing reagent, and
   d) cyclizing the peptide on-resin by means of disulfide bond formation.

2. Method according to claim 1, characterized in that said cysteine is at least 3 amino acid residues spaced apart from the N-terminal amino acid residue of said peptide.

3. Method according to claim 1, characterized in that the solid phase resin is selected from 2-chloro-trityl (CTC) or an amide-producing resin.

4. Method according to claim 1, characterized in that the removal of at least the S-tert.butyl-sulphenyl group is accomplished by reacting the peptide with a trialkylphosphine.

5. Method according to claim 1, characterized in that the peptide is cyclized in the presence of a weak base in a polar, aprotic solvent.

6. Method according to claim 1, characterized in that the linkage of the peptide to the solid phase is labile in 60% TFA in dichloro-methane at room temperature.

7. Method according to claim 1, characterized in that the resin is a Sieber resin.

8. Method according to claim 1, characterized in that in a subsequent step, the peptide is cleaved off from the resin.

9. Peptide of formula I

I

[Chemical structure of cyclic peptide with substituents NR4, NHR5, NH, R1, R2, R3]

wherein R4 and R5 are H or an Arg-protection group, R2 is a carboxylic acid protection group and R3 is a Trp-protection group and R1 is a solid phase in a thioester, ester or amide bond linkage to the peptide backbone, with the proviso, that said bond linkage is not a benzylester bond linkage, but is an acid-labile bond linkage that is cleaved under weakly acidic reaction conditions.

10. Peptide according to claim 9, characterized in that R4 and R5 are H and R3 is N-benzyl-oxycarbonyl and R2 is tertiary-butyl.

11. Peptide according to claim 10, characterized in that the solid phase is a Sieber resin which is consequently in amide bond linkage to the peptide backbone.

12. Peptide wherein the peptide is linked to a solid phase via the C-terminal residue, characterised in that the peptide is a cyclic peptide comprising a moiety of formula II

II $$N\alpha—\overset{O}{\overset{\|}{C}}—[CH_2]_n—S—S—[CH_2]_m—C^*H(—R5)(—NH—R6)$$

wherein n is 2 and m is 1, Nα is the N-terminal nitrogen of the peptide backbone and C* is the Cα of a C-terminal Cys residue of the peptide backbone, with R6 being the N-terminal, cyclic half of the peptide backbone that is terminating with said Nα and R5 being the carboxy group of said C-terminal Cys residue that is linked to the solid phase by means of an ester or amide bond to the solid phase, with the proviso, that said linking bond is not a benzylester bond, but is an acid-labile bond that is cleaved under weakly acidic reaction conditions, with the proviso that N≠Nα.

13. Peptide which is linked to a solid phase via the C-terminal residue by means of an ester or amide bond to the solid phase, with the proviso, that said linking bond is not a benzylester bond, but is an acid-labile bond that is cleaved under weakly acidic reaction conditions, characterised in that said C-terminal residue is a cysteine, homo- or nor-cysteine residue that is protected in its side chain by a S-tert.butyl-sulphenyl group and which is N-terminally substituted at its Nα to constitute the amide moiety of formula III

III $$HOOC—[CH_2]_n—S—S—[CH_2]_n—\overset{O}{\overset{\|}{C}}—N\alpha$$

wherein n=2.

14. Peptide which is linked to a solid phase via the C-terminal residue by means of an ester or amide bond to the solid phase, with the proviso, that said linking bond is not a benzylester bond, but is an acid-labile bond that is cleaved under weakly acidic reaction conditions, characterised in that said C-terminal residue is a cysteine, homo- or nor-cysteine residue that has a free thiol group in its side chain and which is N-terminally substituted at its Nα to constitute the amide moiety of formula III

III $$HOOC—[CH_2]_n—S—S—[CH_2]_n—\overset{O}{\overset{\|}{C}}—N\alpha$$

wherein n=1 to 10.

15. The method of claim 2 wherein said cysteine is at least 5 amino acid residues spaced apart from the N-terminal amino acid residue of said peptide.

16. The method of claim 8 wherein the peptide is cleaved from the resin under conditions of global deprotection.

17. The peptide of claim 12 further comprising at least one amino acid side chain protecting group.

18. The peptide of claim 12, wherein R6 of formula II further comprises at least 3 intervening amino acid residues.

19. The peptide of claim 12, wherein R6 of formula II further comprises at least 4 intervening amino acid residues.

20. The peptide of claim 13 further comprising at least one amino acid side chain protection group other than a S-tert.butyl-sulphenyl group on a cysteine, homo- or nor-cysteine residue.

21. The peptide of claim 14 further comprising at least one amino acid side chain protection group other than a S-tert.butyl-sulphenyl group on a cysteine, homo- or nor-cysteine residue.

22. The method of claim 1 wherein in step (d) cyclizing the peptide is performed in the presence of air and/or oxygen.

* * * * *

SEQUENCE LISTING

```
<160> NUMBER OF SEQ ID NOS: 3

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Mercaptopropionic acid
<220> FEATURE:
<221> NAME/KEY: DISULFID
<222> LOCATION: (1)..(7)
<220> FEATURE:
<221> NAME/KEY: MOD_RES
<222> LOCATION: (2)..(2)
<223> OTHER INFORMATION: Homoarginine
<220> FEATURE:
<223> OTHER INFORMATION: C-term -NH2

<400> SEQUENCE: 1

Xaa Arg Gly Asp Trp Pro Cys
 1               5

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Mercaptopropionic acid
<220> FEATURE:
<221> NAME/KEY: DISULFID
```

```
<222> LOCATION: (1)..(7)
<220> FEATURE:
<221> NAME/KEY: MOD_RES
<222> LOCATION: (2)..(2)
<223> OTHER INFORMATION: Homoarginine
<220> FEATURE:
<221> NAME/KEY: MOD_RES
<222> LOCATION: (4)..(4)
<223> OTHER INFORMATION: Asp(tBu)
<220> FEATURE:
<221> NAME/KEY: MOD_RES
<222> LOCATION: (5)..(5)
<223> OTHER INFORMATION: Trp(Boc)
<220> FEATURE:
<223> OTHER INFORMATION: C-term -NH

<400> SEQUENCE: 2

Xaa Arg Gly Asp Trp Pro Cys
1               5

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Mercaptopropionic acid
<220> FEATURE:
<221> NAME/KEY: MOD_RES
<222> LOCATION: (3)..(3)
<223> OTHER INFORMATION: Homoarginine
<220> FEATURE:
<221> NAME/KEY: MOD_RES
<222> LOCATION: (5)..(5)
<223> OTHER INFORMATION: Asp(tBu)
<220> FEATURE:
<221> NAME/KEY: MOD_RES
<222> LOCATION: (6)..(6)
<223> OTHER INFORMATION: Trp(Boc)
<220> FEATURE:
<221> NAME/KEY: MOD_RES
<222> LOCATION: (8)..(8)
<223> OTHER INFORMATION: Cys(S-tBu)
<220> FEATURE:
<223> OTHER INFORMATION: C-term -NH

<400> SEQUENCE: 3

Xaa Xaa Arg Gly Asp Trp Pro Cys
1               5
```